United States Patent [19]

Ross et al.

[11] 4,158,659

[45] Jun. 19, 1979

[54] ACYLAMINO DERIVATIVES

[75] Inventors: William J. Ross, Lightwater; John P. Verge, Henley-on-Thames; William R. N. Williamson, Slough, all of England

[73] Assignee: Lilly Industries Limited, London, England

[21] Appl. No.: 840,345

[22] Filed: Oct. 7, 1977

Related U.S. Application Data

[63] Continuation of Ser. No. 691,962, Jun. 1, 1976, abandoned.

[30] Foreign Application Priority Data

Jun. 5, 1975 [GB] United Kingdom ............... 24224/75

[51] Int. Cl.² .................. C07D 271/10; C07D 285/12; A61K 31/42; A61K 31/425
[52] U.S. Cl. ......................... 260/307 G; 260/306.8 D; 260/554; 424/270; 424/272
[58] Field of Search ..................... 260/306.8 D, 307 G

[56] References Cited

U.S. PATENT DOCUMENTS

| | | | |
|---|---|---|---|
| 3,141,022 | 7/1964 | Piala et al. | 260/307 G |
| 3,728,354 | 4/1973 | Rucker et al. | 260/306.8 D |
| 3,880,873 | 4/1975 | Doyle et al. | 260/306.8 D |

FOREIGN PATENT DOCUMENTS

| | | | |
|---|---|---|---|
| 1230432 | 5/1971 | United Kingdom | 260/306.8 D |
| 1264011 | 2/1972 | United Kingdom | 260/306.8 D |
| 1333495 | 10/1973 | United Kingdom | 260/306.8 D |
| 1396941 | 6/1975 | United Kingdom | 260/306.8 D |

OTHER PUBLICATIONS

Neville et al., Derwent No. 43048w, 6/19/75.
Selim et al., Bull. Soc. Chim. Fr. 1967, pp. 1219–1220.

*Primary Examiner*—Alton D. Rollins
*Attorney, Agent, or Firm*—Nancy J. Harrison; Everet F. Smith

[57] ABSTRACT

Acylamino heteroaryl compounds in which the heteroaryl nucleus is a 1,3,4-oxadiazole or 1,3,4-thiadiazole nucleus, methods of making the compounds and pharmaceutical formulations containing the compounds. The compounds have anti-allergy activity.

6 Claims, No Drawings

ACYLAMINO DERIVATIVES

This is a continuation of application Ser. No. 691,962, filed June 1, 1976, now abandoned.

This invention relates to heterocyclic chemical compounds, more particularly to certain novel 5-membered heteroaryl derivatives substituted by an acylamino group which are useful for the chemotherapy of immediate hypersensitivity conditions and/or which are useful as intermediates in the preparation of such active compounds. The invention also includes processes for preparing the active compounds of the invention. Furthermore, the invention includes within its scope pharmaceutical compositions containing pharmacologically active compounds and methods of treatment of animals, including humans, comprising administering thereto an effective dose of the compound or compounds or of pharmaceutical compositions comprising the active compound or compounds of the invention.

Compounds similar to those of the present invention have been previously described, see, for example, Belgian Pat. No. 736854 and U.K. Pat. No. 1,333,495, as herbicides.

It is an object of the present invention to provide compounds useful in the chemotherapy of immediate hypersensitivity conditions.

According to the present invention there is provided a compound of formula (I):

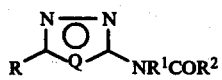

(I)

wherein:

(A) Q represents a sulphur atom; R is $C_{1-4}$ alkyl or phenyl; $R^1$ is $C_{4-8}$ alkyl, $C_{3-6}$ alkenyl, $C_{3-8}$ cycloalkyl or benzyl optionally substituted by $C_{1-3}$ alkyl or halogen and $R^2$ is $C_{1-6}$ alkyl, $C_{3-8}$ cycloalkyl, phenyl or benzyl; or (B) Q represents an oxygen atom; R is $C_{1-4}$ alkyl or phenyl; $R^1$ is $C_{1-6}$ alkyl, $C_{3-6}$ alkenyl, $C_{3-8}$ cycloalkyl or benzyl optionally substituted by $C_{1-3}$ alkyl or halogen and $R^2$ is $C_{1-6}$ alkyl, $C_{3-8}$ cycloalkyl, phenyl or benzyl.

The two systems represented by formula (I) are the 1,3,4-oxadiazole and 1,3,4-thiadiazole systems of formula:

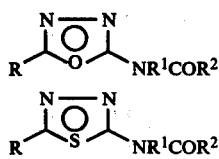

(II)

(III)

Particularly interesting compounds of formula (I) to (III) are those wherein R is a $C_{1-4}$ alkyl group, especially methyl, $R^1$ is $C_{1-6}$ alkyl, especially $C_{4-6}$ alkyl, $C_{3-5}$ alkenyl or benzyl and $R^2$ is $C_{3-6}$ alkyl, $C_{3-6}$ cycloalkyl or benzyl.

The compounds of formula (I) to (III) may be prepared by:

(a) acylating an alkyl derivative of formula (VIII):

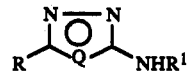

(VIII)

wherein R, Q and $R^1$ are as previously defined; or (b) alkylating an acyl derivative of formula (IX):

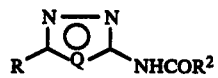

(IX)

where R, Q and $R^2$ are as previously defined.

The acylation of the compound of formula (VIII) may be carried out with an acid halide having the formula $R^2CO$-X wherein X is chlorine or bromine and $R^2$ is defined above in the presence of a proton acceptor, such as pyridine or triethylamine, in an inert solvent, such as benzene. The acylation may also be carried out by heating the alkyl derivative with a suitable acid anhydride, $(R^2CO)_2O$, in an inert solvent.

Those skilled in the art will immediately appreciate that a wide variety of other acylating conditions can be used (see, for example, "The Chemistry of Amides" 1971 by A. J. Beckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser, etc.).

Compounds of formula (IX) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula $R^1X^1$ where $X^1$ is a reactive atom such as a halogen atom or a reactive group such as an alkyl sulphate group.

Alkylating agents and alkylating reaction conditions other than those specified above can be utilised, the nature of these being readily apparent to those acquainted with the art.

The derivatives of formulae (VIII) and (IX) can be derived from the corresponding primary amines by standard alkylation or acylation techniques. Such amines are either known compounds or can be prepared by modification of known synthetic methods.

According to a further aspect of the present invention there is provided a pharmaceutical formulation which comprises as active ingredient a chemotherapeutically effective amount of a compound of formula (I):

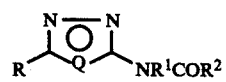

(I)

wherein Q represents an oxygen or sulphur atom; R is $C_{1-4}$ alkyl or phenyl; $R^1$ is $C_{1-8}$ alkyl, $C_{3-6}$ alkenyl, $C_{3-8}$ cycloalkyl or benzyl optionally substituted by $C_{1-3}$ alkyl or halogen and $R^2$ is $C_{1-6}$ akyl, $C_{3-8}$ cycloalkyl, phenyl or benzyl; associated with a pharmaceutically acceptable carrier therefor.

Compounds of formula (I) have been shown to be useful in the prophylactic and therapeutic treatment of immediate hypersensitivity diseases including asthma and in the alleviation of *status asthmaticus*. The compounds have low toxicity.

The compounds or formulations of the present invention may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

Preferred pharmaceutical forms of the present invention are capsules, tablets, suppositories, aerosols, injectible solutions, cremes and ointments.

The following Examples will further illustrate the invention.

EXAMPLE 1

N-Methyl-N-(5-methyl-1,3,4-thiadiazol-2-yl)-benzamide 2-(N-Methyl-amino)-5-methyl-1,3,4-thiadiazole (6 g, 0.046 mole) in pyridine (190 ml) was refluxed for 6 hours with benzoyl chloride (9.7 g, 0.069 mole) and the pyridine then evaporated off under reduced pressure. The residue was treated with water, made alkaline with sodium hydroxide solution and extracted with chloroform. The chloroform was washed with a saturated solution of sodium bicarbonate and a saturated solution of sodium chloride, dried, filtered and evaporated to yield title product which was recrystallised from ethanol.

EXAMPLE 2

N-2-Propenyl-N-(5-methyl-1,3,4-thiadiazol-2-yl)-benzamide

Using the process of Example 1, the title compound was prepared from 2-[N-(2-propenyl)-amino]-5-methyl-1,3,4-thiadiazole, which had been prepared by cyclisation from 4-(2-propenyl)-thiosemicarbazide.

EXAMPLE 3

N-Phenylmethyl-N-(5-methyl-1,3,4-thiadiazol-2-yl)-benzeneacetamide (a) N-(5-Methyl-1,3,4-thiadiazol-2-yl)-benzylamine 2-Amino-5-methyl-1,3,4-thiadiazole (23 g, 0.2 mole) and benzaldehyde (29.6 ml, 0.3 mole) were refluxed together in ethanol (200 ml) for 1½ hours. The solution was cooled to room temperature and sodium borohydride (11.35 g, 0.3 mole) added over 5 to 10 minutes. The mixture was refluxed for 4 hours, treated with further sodium borohydride (5 g) and refluxed overnight. The ethanol was evaporated off, the residue treated with water and extracted with ether. The ether extract was dried over sodium sulphate, filtered and evaporated to leave an oil which solidified. This solid was triturated with ether, filtered, washed with light petroleum (b.p. 40°–60° C.) and again triturated with ether and filtered to give N-(5-methyl-1,3,4-thiadiazol-2-yl)-benzylamine (30.95 g), which on recrystallisation from ether had m.p. 140° C.

(b) N-Phenylmethyl-N-(5-Methyl-1,3,4-thiadiazol-2-yl)-benzene acetamide

N-(5-Methyl-1,3,4-thiadiazol-2-yl)-benzylamine (15 g, 0.073 mole) in pyridine (200 ml) was refluxed with phenylacetyl chloride for 6 hours. The pyridine was removed under educed pressure and the residue treated with water and extracted with ether. The ethereal solution was dried, filtered and evaporated to dryness and the residue recrystallised from ethanol to give the title compound, m.p. 128° C.

EXAMPLES 4 TO 6

The following compounds were prepared by similar methods to that described in Example 3:

N-(p-Chlorobenzyl)-N-(5-methyl-1,3,4-thiadiazol-2-yl)-benzamide

N-o-Chlorophenylmethyl-N-(5-methyl-1,3,4-thiadiazol-2-yl)-benzeneacetamide

N-(p-Methylbenzyl)-N-(5-phenyl-1,3,4-thiadiazol-2-yl)-cyclopentanecarboxamide

EXAMPLE 7

N-Hexyl-N-(5-methyl-1,3,4-thiadiazol-2-yl)-benzeneacetamide (a) N-(5-Methyl-1,3,4-thiadiazol-2-yl)-hexanamide 2-amino-5-methyl-1,3,4-thiadiazole (23 g, 0.2 mole) in toluene (100 ml) was treated with n-hexanoic anhydride (50 ml) and the mixture was refluxed for 3 hours. The product crystallised on standing at room temperature overnight. The product was filtered off and recrystallised from ethyl acetate to give N-(5-methyl-1,3,4-thiadiazol-2-yl)-hexanamide, m.p. 203° C. (20.68 g).

(b) N-(5-Methyl-1,3,4-thiadiazol-2-yl)-hexylamine

N-(5-Methyl-1,3,4-thiadiazol-2-yl)-hexanamide (16 g, 0.075 mole) was added portionwise to stirred tetrahydrofuran (THF) (120 ml) containing lithium aluminium hydride (2.9 g, 0.076 mole) at a temperature below 15° C. The mixture was stirred and refluxed for 2 hours. The mixture was cooled in ice and treated with water (2.9 ml) in THF (29 ml) followed by a 2 N solution of sodium hydroxide (2.9 ml) and water (5.8 ml). The mixture was then treated with 'Supercel' and filtered. The filtrate was evaporated to give the title product which was recrystallised from 50% aqueous methanol (9.5 g) m.p. 101°–105° C.

(c) N-Hexyl-N-(5-methyl-1,3,4-thiadiazol-2-yl)-benzeneacetamide

N-(5-Methyl-1,3,4-thiadiazol-2-yl)-hexylamine (5.98 g, 0.03 mole) in toluene (60 ml) was stirred together with triethylamine (4.59 ml) and phenylacetyl chloride (4.64 g, 0.03 mole) and refluxed overnight. Further triethylamine (4.6 ml) and phenylacetyl chloride (4 ml) were added and refluxing was continued for a further 24 hours. The mixture was evaporated to dryness, treated with water and extracted with chloroform. The chloroform extract was washed with 2 N sodium hydroxide solution and with water, and was dried (Na$_2$SO$_4$), filtered and evaporated to yield the title product as an oil, b.p. 190° C./0.1 mm (8.03 g). This was recrystallised from ethanol to give the title compound as a solid, m.p. 90° C.

EXAMPLE 8

N-(5-methyl-1,3,4-thiadiazol-2-yl)-2-methylpropanamide

2-Amino-5-methyl-1,3,4-thiadiazole (15 g, 0.13 mole) was treated with isobutyric anhydride (70 ml). The reaction mixture was stirred and heated to reflux in an oil bath at 180°–200° C. for 1½ hours. The excess anhydride was distilled off under reduced pressure and the solid residue was recrystallised from ethyl acetate to give N-(5-methyl-1,3,4-thiadiazole-2-yl)-2-methylpropanamide as golden needles.

EXAMPLES 9 AND 10

The following compounds were similarly prepared:

N-(5-Methyl-1,3,4-thiadiazol-2-yl)butanamide. (m.p. 231°–233° C.)

Cream crystalline solid.

N-(5-methyl-1,3,4-thiadiazol-2-yl)heptanamide

Cream crystalline solid.

EXAMPLE 11

N-(5-methyl-1,3,4-thiadiazol-2-yl)butylamine

N-(5-methyl-1,3,4-thiadiazol-2-yl)butanamide (1.85 g, 0.01 mole) was added in small portions to a stirred suspension of LiAlH$_4$ (0.38 g, 0.01 mole) in dry THF (25 ml) at 0°–5° C. under a nitrogen atmosphere. The reaction mixture was stirred and heated to reflux for 2 hours. The cooled solution was then treated dropwise with a solution of water (0.38 ml) in THF (3.8 ml) followed by 2 N sodium hydroxide solution (0.38 ml) followed by water (0.76 ml) and stirred for ½ hour. The mixture was filtered through a pad of supercel and the solution evaporated under reduced pressure to give a solid which was recrystallised from aqueous ethanol to give N-(5-methyl-1,3,4-thiadiazol-2-yl)butylamine as a pale yellow crystalline solid. m.p. 100°–102° C.

EXAMPLE 12

The following compound was similarly prepared.

N-(5-methyl-1,3,4-thiadiazol-2-yl)heptylamine

EXAMPLE 13

N-Butyl-N-(5-methyl-1,3,4-thiadiazol-2-yl)-2-methylpropanamide

N-(5-methyl-1,3,4-thiadiazol-2-yl)butylamine (3 g, 0.0175 mole) and isobutyric anhydride (15 ml) were heated together on the steam bath for 1½ hours. The excess isobutyric anhydride was removed under reduced pressure and the residue distilled at 0.3 mm. to give an oil (3.6 g, 55%) b.p. 132° C. which gave the title compound as a white solid (m.p. 54°–57° C.) on cooling.

The following compounds were similarly prepared.

EXAMPLES 14 AND 15

N-Hexyl-N-(5-methyl-1,3,4-thiadiazol-2-yl)-2-methylpropanamide

This was a colourless oil b.p. 152°–154° C. at 0.5 mm. $\eta_{21}$ 1.5108 NMR, IR and UV supported the structure.

Analysis: C$_{13}$H$_{23}$N$_3$OS requires: C 57.99; H 8.55; N 15.61%. Found: C 57.81; H 8.67; N 15.76%.

N-Heptyl-N-(5-methyl-1,3,4-thiadiazol-2-yl)-2-methylpropanamide

EXAMPLE 16

N-Butyl-N-(5-methyl-1,3,4-thiadiazol-2-yl)cyclopropane carboxamide

N-(5-methyl-1,3,4-thiadiazol-2-yl)butylamine (1.7 g, 0.01 mole) in benzene (20 ml) was treated with triethylamine (1.53 ml) and cyclopropane carboxylic acid chloride (1.15 g). The reaction mixture was heated to reflux for 20 hours. The solution was then evaporated to dryness and the residue treated with ether and filtered. The solution was washed with water, dried and charcoaled, filtered and evaporated and the residue recrystallised from petrol ether (40°–60° C.) to give N-butyl-N-(5-methyl-1,3,4-thiadiazol-2-yl)cyclopropane carboxamide as a white crystalline solid. m.p. 82°–84° C.

EXAMPLE 17

The following compound was similarly prepared.
N-Butyl-N-(5-methyl-1,3,4-thiadiazol-2-yl)cyclopentane carboxamide This was a colourless oil b.p. 162°–164° C. at 0.4 mm. NMR, IR and UV supported the structure.

Analysis: $C_{13}H_{21}N_3OS$ requires: C 58.4; H 7.9; N 15.7%. Found: C 58.5; H 7.6; N 15.9%.

EXAMPLE 18

N-(5-methyl-1,3,4-thiadiazol-2-yl)-1-methylethylamine

2-Amino-5-methyl-1,3,4-thiadiazole (23 g, 0.2 mole) in IPA (700 ml) and acetone (100 ml) was treated with sodium borohydride (20 g) in portions with stirring and cooling. The reaction mixture was then stirred and heated to reflux for 3½ hours. The solution was then poured into water (3 L) and extracted with ether (× 3). The ethereal solution was dried, filtered and evaporated to give the title compound as a cream solid. m.p. 145° C.

EXAMPLE 19

N-(5-methyl-1,3,4-thiadiazol-2-yl)cyclohexylamine

White crystalline solid (from ethyl acetate) m.p. 192°–194° C. This was prepared by the route described in Example 18.

EXAMPLE 20

N-(1-methylethyl)-N-(5-methyl-1,3,4-thiadiazol-2-yl)benzamide

N-(5-methyl-1,3,4-thiadiazol-2-yl)-1-methylethylamine (5 g, 0.032 mole) in pyridine (100 ml) was treated with benzoyl chloride (4.1 ml). The reaction mixture was stirred and heated to reflux for 5½ hours. The pyridine was removed under reduced pressure and the residue treated with water and extracted with ether (× 3). The ethereal solution was dried, filtered and evaporated to dryness and the residue recrystallised from ether/petrol ether (40°–60° C.) to give the title compound as a pale yellow crystalline solid m.p. 82.5°–83.5° C.

The following compounds were similarly prepared.

EXAMPLES 21 AND 22

N-(1-Methylethyl)-N-(5-methyl-1,3,4-thiadiazol-2-yl)benzene acetamide

This was a buff crystalline solid. m.p. 83°–85° C.

N-Cyclohexyl-N-(5-methyl-1,3,4-thiadiazol-2-yl)cyclopropane carboxamide

This was a yellow crystalline solid m.p. 76.5°–78.5° C.

EXAMPLE 23

N-(5-Methyl-1,3,4-oxadiazol-2-yl)-N-n-propyl cyclobutane carboxamide

(a) 1-Acetyl-4-allyl-semicarbazide

Allyl isocyanate (25 g, 0.30 mol) was added slowly to a boiling solution of acethydrazide (22.2 g, 0.30 mol) in dry benzene (300 ml). The mixture was heated for 1 hour whereupon 2 layers formed. The benzene was then evaporated off and the residue triturated with ether to yield the title compound as a white solid. (m.p. 71°–74° C.).

(b) 5-Methyl-2-n-propylamino-1,3,4-oxadiazole

1-Acetyl-4-n-propyl semicarbazide (35 g, 0.22 mol) prepared by method (a) above, was refluxed with $POCl_3$ (150 ml) for 2 hours, until no more HCl was evolved. Excess $POCl_3$ was taken off by a water pump and the mixture poured into 200 ml. iced water and neutralized with 50% NaOH to pH 7. Red oil was extracted with dichloromethane (2×180 ml), dried, filtered and evaporated down to yield an oil which was distilled in a vigreux flask to yield the title compound as a pink liquid which crystallised upon standing to a solid. (m.p. 46.5°–47.5° C.).

(c) N-(3-Methyl-1,3,4-oxadiazol-2-yl)-N-n-propyl cyclobutane carboxamide

5-Methyl-2-n-propylamino 1,3,4-oxadiazole (6 g, 0.04 mol) prepared as in (b) above, was refluxed with cyclobutanecarboxylic acid chloride (5.5 g, 0.05 mol) in benzene (25 ml) in the presence of triethylamine (4.72 g, 0.05 mol) for 2 hours. The mixture was filtered and the filtrate washed with dilute HCl, saturated solution $NaHCO_3$ and water; dried over magnesium sulphate, filtered, solvent evaporated off to yield a reddish brown liquid which was distilled twice in a vigreux flask to yield the title compound as a slightly pink liquid (b.p. 110°–111° C./0.27 mm Hg).

EXAMPLES 24 TO 31

Using the procedure described in Example 23 the following further oxadiazoles were prepared:

N-(5-Methyl-1,3,4-oxadiazol-2-yl)-N-n-propyl 2-methylpropanamide (b.p. 85°–87° C./0.4 mm Hg).

N-(5-Methyl-1,3,4-oxadiazol-2-yl)-N-n-propyl cyclohexane carboxamide (b.p. 120°–121° C./0.2 mm Hg).

N-(5-Methyl-1,3,4-oxadiazol-2-yl)-N-n-propyl cyclopentane carboxamide (b.p. 110°–112° C./0.01 mm Hg).

N-(5-Methyl-1,3,4-oxadiazol-2-yl)-N-2-propenyl-2-methylpropanamide (b.p. 93° C./0.18 mm Hg).

N-(5-Methyl-1,3,4-oxadiazol-2-yl)-N-2-cyclopentane carboxamide (b.p. 114°–116° C./0.12 mm Hg).

N-(5-Methyl-1,3,4-oxadiazol-2-yl)-N-n-hexyl-n-hexanamide (b.p. 116° C./0.1 mm Hg).

N-(5-Methyl-1,3,4-oxadiazol-2-yl)-N-n-butyl-2-methylpropanamide (b.p. 82°–84° C./0.1 mm Hg).

N-(5-Methyl-1,3,4-oxadiazol-2-yl)-N-n-butylacetamide (b.p. 82°–84° C./0.1 mm Hg).

The following Examples 32 to 39 illustrate pharmaceutical formulations containing the active compound N-(5-methyl-1,3,4-oxadiazol-2-yl)-N-2-propenyl-2-methylpropanamide.

EXAMPLE 32

Soft gelatin capsules were prepared using the following ingredients:

|  | Quantity (mg/capsule) |
| --- | --- |
| Active compound | 30 |
| Butylated hydroxyanisole B.P. | 0.02 |
| Fractionated Coconut Oil B.P.C. | 70 |
|  | 100.02 |

The above ingredients were mixed and filled into soft gelatin capsules, the main shell components of which were gelatin and glycerine.

EXAMPLE 33

The procedure of Example 32 was repeated except that an identical quantity of propyl gallate was used in place of the butylated hydroxyanisole as antioxidant.

EXAMPLE 34

Hard gelatin capsules were prepared using the following ingredients:

|  | Quantity(mg/capsule) |
|---|---|
| Active compound | 23 |
| Silicon dioxide (fumed) | 23 |
| Lactose | 48 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 35

An ointment was made up from the following ingredients:

| Active compound | 1.5% by weight |
|---|---|
| Butylated hydroxyanisole B.P. | 0.02% by weight |
| White soft paraffin | q.s. 100% |

The hydroxyanisole was dissolved in the melted paraffin and the active compound then added in, and the mixture allowed to cool.

EXAMPLE 36

A topical cream containing 1.0% of the compound is prepared as follows:

|  | grams |
|---|---|
| Active compound | 1.0 |
| Cetomacrogol 1000 | 3.0 |
| Cetostearyl alcohol | 11.5 |
| Liquid Paraffin | 9.0 |
| Butylated hydroxyanisole B.P. | 0.02 |
| Distilled water | to 100.0 |

The compound was mixed with the hydroxyanisole and suspended in the liquid paraffin. The cetostearyl alcohol was added and the mixture heated to 70° C. with stirring. The cetomacrogol 1000 was dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 37

Suppositories containing 30 and 60 mg. of the compound were prepared as follows:

| Active compound | 3 g. |
|---|---|
| Henkel base | 97 g. |

The active compound was mixed with the Henkel base which had been previously melted using the minimum amount of heat possible. The mixture was then poured into suppository moulds of a nominal capacity of 1 g. or 2 g. as desired, to produce suppositories each containing 30 mg. or 60 mg. of the active compound.

EXAMPLE 38

An aerosol was prepared containing the following ingredients:

|  | Quantity per ml. |
|---|---|
| Active compound | 10.00 mg. |
| Propylene glycol | 10.00 mg. |
| Dichlorotetrafluoroethane (Propellant 114) | 550.00 mg. |
| Dichlorodifluoromethane (Propellant 12) | 830.00 mg. |

The active compound was mixed with the propylene glycol and the mix added to the propellant 114, the mixture cooled to −15° to −20° C. and transferred to a filling device. At the same time a mixture of propellants 114 and 12, previously cooled to −15° to −20° C. was fed into a second filling device. A metered amount of propellant from the second filling device was introduced into a stainless steel container, followed by the required amount of material from the first filling device. The valve units were then fitted and sealed to the container. These valve units were equipped with a metering device so that approximately 0.15 mg. of the active compound is released by a single actuation of the valve.

EXAMPLE 39

Tablets were prepared using the following components:

| Active compound | 10.00 mg. |
|---|---|
| Microcrystalline Cellulose | 250.00 mg. |
| Sodium Carboxymethyl Starch | 25.00 mg. |
| Magnesium Stearate | 3.00 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and then the magnesium stearate was mixed in. Finally, the mixture was compressed to form tablets.

In the foregoing Examples 32 to 39, the liquid active compound used may, in accordance with the invention, be replaced wholly or in part by other liquid active compounds of formula I. If the active compound is a solid, appropriate modification will of course have to be made.

We claim:

1. A compound of the formula

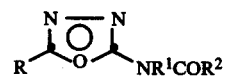

wherein:
R is $C_{1-4}$ alkyl; $R^1$ is $C_{1-6}$ alkyl, $C_{3-6}$ alkenyl, $C_{3-8}$ cycloalkyl or benzyl optionally substituted by $C_{1-3}$ alkyl or halogen and $R^2$ is $C_{1-6}$ alkyl, $C_{3-8}$ cycloalkyl, phenyl or benzyl.

2. A compound of claim 1 wherein $R^1$ represents $C_{1-6}$ alkyl, $C_{3-5}$ alkenyl or benzyl and $R^2$ represents $C_{3-6}$ alkyl, $C_{3-6}$ cycloalkyl or benzyl.

3. A compound of claim 2 wherein $R^1$ represents $C_{4-6}$ alkyl.

4. The compound of claim 1 which is N-(5-methyl-1,3,4-oxadiazol-2-yl)-N-(n-propyl)cyclobutane carboxamide.

5. The compound of claim 1 which is N-(5-methyl-1,3,4-oxadiazol-2-yl)-N-(2-propenyl)-2-methylpropanamide.

6. The compound of claim 1 which is N-(5-methyl-1,3,4-oxadiazol-2-yl)-N-(n-butyl)acetamide.

* * * * *